United States Patent
Mercer et al.

(10) Patent No.: US 9,212,981 B2
(45) Date of Patent: Dec. 15, 2015

(54) FEEDBACK SYSTEM AND METHOD FOR ASSESSING FIXATION AND STABILITY OF IMPLANTABLE LEADS

(71) Applicant: Purdue Research Foundation, West Lafayette, IN (US)

(72) Inventors: Elizabeth Mercer, Zionsville, IN (US); Johnny Zhang, West Lafayette, IN (US); Joseph Michael Pellettiere, Long Grove, IL (US); Jason Wenhaw Lee, Vernon Hills, IL (US)

(73) Assignee: Purdue Research Foundation, West Lafayette, IN (US)

( * ) Notice: Subject to any disclaimer, the term of this patent is extended or adjusted under 35 U.S.C. 154(b) by 101 days.

(21) Appl. No.: 14/099,953

(22) Filed: Dec. 7, 2013

(65) Prior Publication Data

US 2014/0165738 A1 Jun. 19, 2014

Related U.S. Application Data

(60) Provisional application No. 61/734,563, filed on Dec. 7, 2012.

(51) Int. Cl.
*A61F 11/00* (2006.01)
*G01N 3/08* (2006.01)
(Continued)

(52) U.S. Cl.
CPC *G01N 3/08* (2013.01); *A61N 1/057* (2013.01); *G01M 99/007* (2013.01);
(Continued)

(58) Field of Classification Search
CPC . G01N 19/04; G01N 2203/0017; G01N 3/04; G01N 3/08; A61N 1/057; A61N 1/05; A61N 2001/0578; A61B 2019/464; A61B 17/3468

USPC ........... 73/856, 859, 860, 826, 830, 831, 833, 73/834, 150 A, 150 R, 862; 606/1, 129, 606/108; 607/127, 116, 128
See application file for complete search history.

(56) References Cited

U.S. PATENT DOCUMENTS 4,705,042 A 11/1987 Giurtino
4,830,005 A 5/1989 Woskow
(Continued)

OTHER PUBLICATIONS

Biotronik, "ERA 300 Pacing System Analyzer" Manual, Biotronik, Inc., Berlin Germany.
(Continued)

*Primary Examiner* — Lisa Caputo
*Assistant Examiner* — Jonathan Dunlap
(74) *Attorney, Agent, or Firm* — Purdue Research Foundation

(57) ABSTRACT

A lead fixation and stability feedback assembly for testing stability and anchoring of a fixation tip of a distal end of an implantable lead to a tissue is disclosed. The assembly includes a first member including a first coupling arrangement configured to couple to a proximal end of an implantable lead, wherein the proximal end of the implantable lead is coupled to a distal end of the implantable lead configured to be anchored to a tissue, and a second member including a second coupling arrangement configured to couple the first member to the second member, the second coupling arrangement configured to decouple the second member from the first member when a predetermined force is applied to pull the second member away from the first member to thereby test the anchoring of the distal end of the implantable lead to the tissue.

18 Claims, 13 Drawing Sheets

(51) Int. Cl.
*G01M 99/00* (2011.01)
*G01N 19/04* (2006.01)
*A61B 19/00* (2006.01)
*A61N 1/05* (2006.01)
*G01N 3/04* (2006.01)
*A61B 17/34* (2006.01)

(52) U.S. Cl.
CPC ...... *A61B 17/3468* (2013.01); *A61B 2019/464* (2013.01); *A61N 1/05* (2013.01); *A61N 2001/0578* (2013.01); *G01N 3/04* (2013.01); *G01N 19/04* (2013.01); *G01N 2203/0017* (2013.01)

(56) References Cited

U.S. PATENT DOCUMENTS

| | | | |
|---|---|---|---|
| 4,848,346 A | | 7/1989 | Crawford |
| 5,549,615 A | * | 8/1996 | Hocherl et al. ............... 606/108 |
| 5,741,311 A | | 4/1998 | Venes |
| 6,763,270 B1 | | 7/2004 | Gomperz et al. |
| 8,100,021 B2 | * | 1/2012 | Sykes ............................. 73/827 |
| 8,428,747 B2 | * | 4/2013 | Coe et al. ....................... 607/116 |
| 9,038,486 B2 | * | 5/2015 | Stoneback ............... 73/862.393 |
| 2009/0234367 A1 | | 9/2009 | Verma |
| 2009/0301216 A1 | * | 12/2009 | Sykes ............................. 73/833 |
| 2010/0082087 A1 | | 4/2010 | Silipo et al. |
| 2012/0172891 A1 | | 7/2012 | Lee |
| 2012/0172892 A1 | | 7/2012 | Grubac et al. |
| 2014/0018818 A1 | * | 1/2014 | Somogyi et al. .............. 606/129 |
| 2014/0150565 A1 | * | 6/2014 | Stoneback ....................... 73/831 |
| 2014/0188140 A1 | * | 7/2014 | Meier et al. .................... 606/148 |
| 2014/0378992 A1 | * | 12/2014 | Ollivier ......................... 606/129 |
| 2015/0051614 A1 | * | 2/2015 | Schmidt et al. ............... 606/129 |

OTHER PUBLICATIONS

Biotronik, "Biotronik introduces new unique Reliaty Pacing System Analyzer" Press Release, Biotronik, Berlin Germany.

de Vaal, "The in vivo Assessment of Mechanical Loadings on Pectoral Pacemaker Implants", Journal of Biomechanics, 2010, 43 (9), 1717-22. South Africa and USA.

* cited by examiner

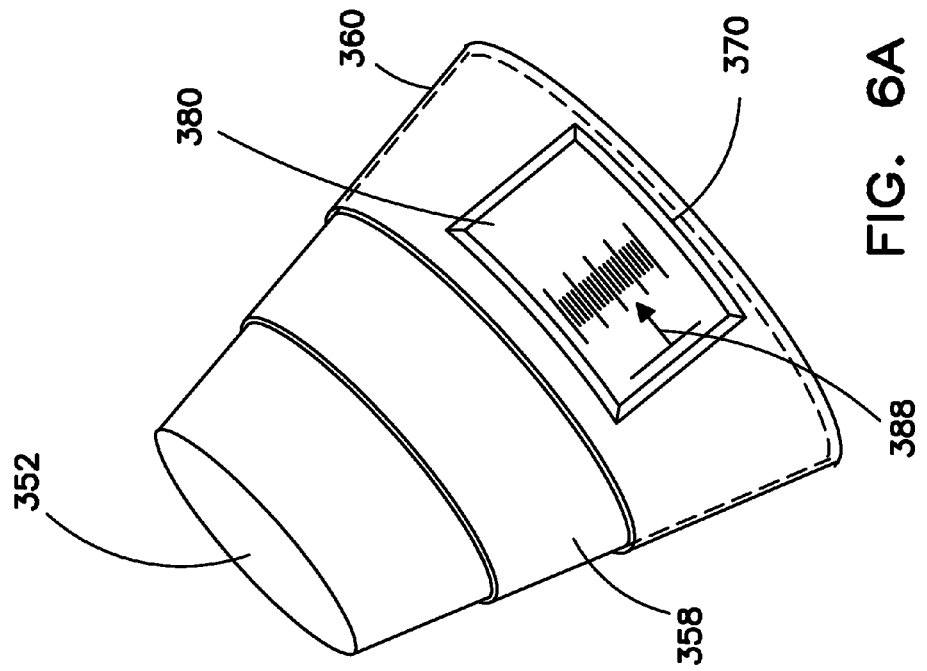
FIG. 6A
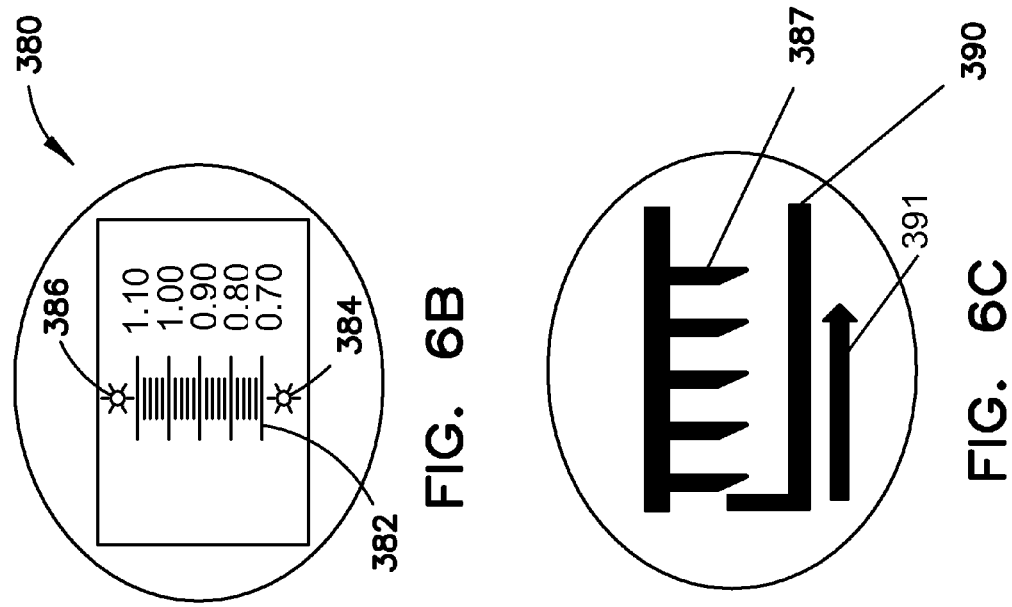
FIG. 6B
FIG. 6C

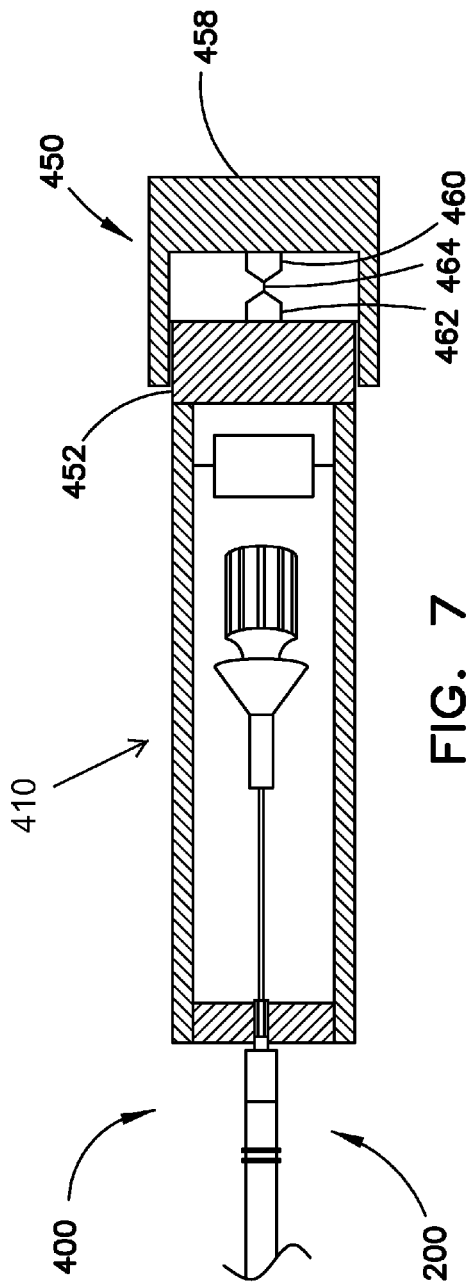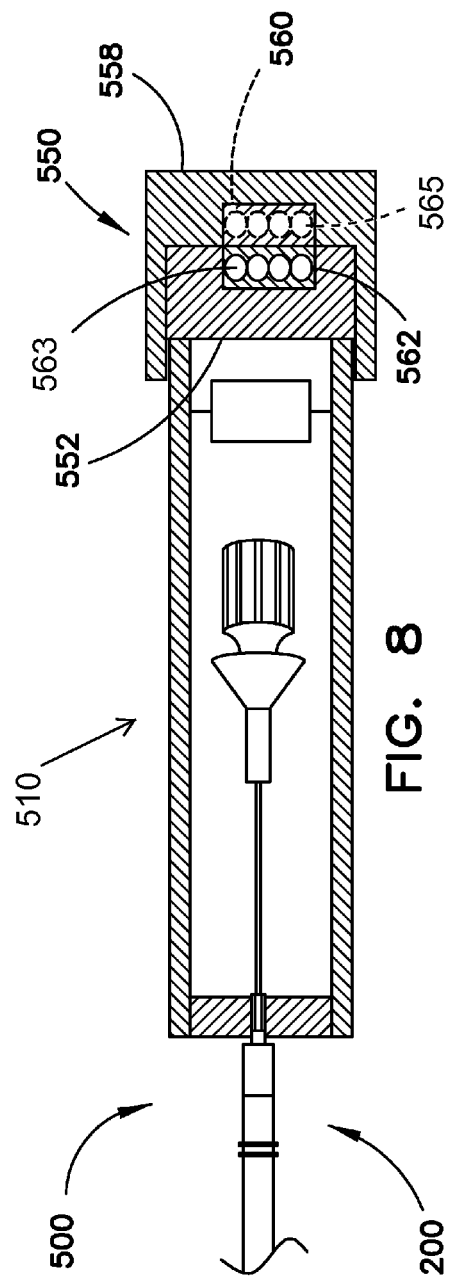

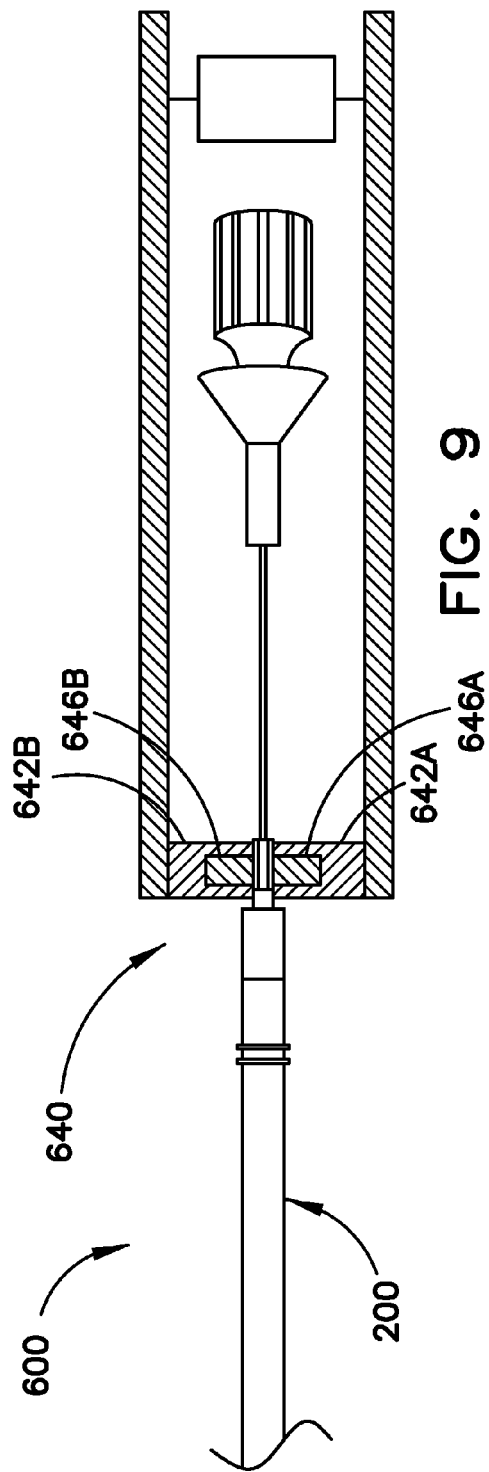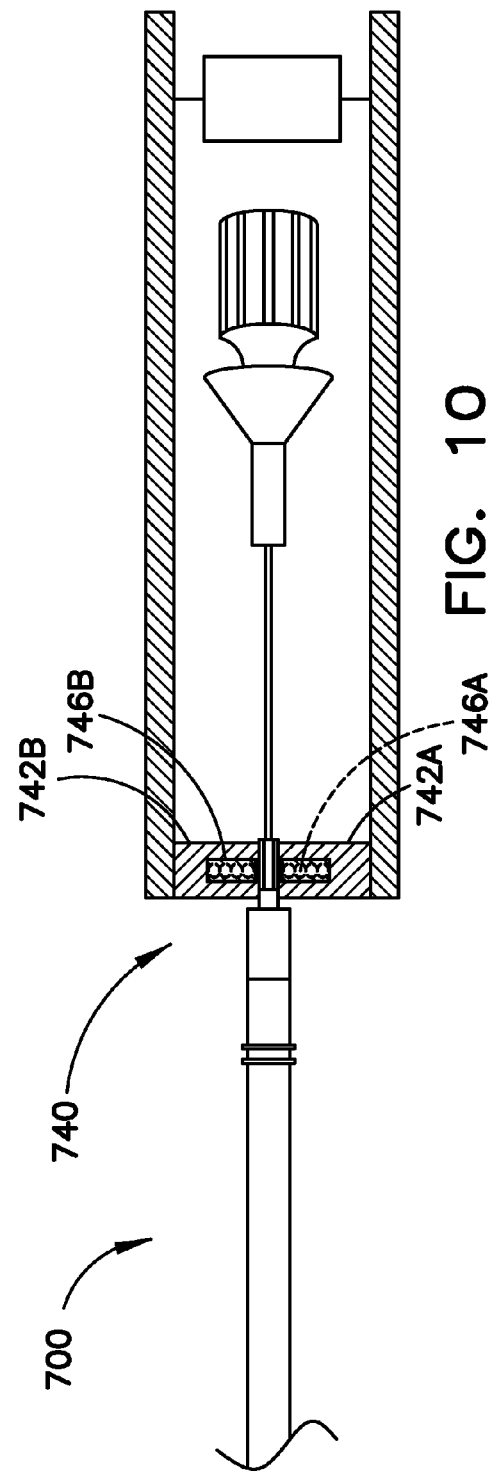

FEEDBACK SYSTEM AND METHOD FOR ASSESSING FIXATION AND STABILITY OF IMPLANTABLE LEADS

CROSS-REFERENCE TO RELATED APPLICATIONS

The present U.S. patent application is related to and claims the priority benefit of U.S. Provisional Patent Application Ser. No. 61/734,563, filed Dec. 7, 2012, the contents of which is hereby incorporated by reference in its entirety into the present disclosure.

STATEMENT REGARDING GOVERNMENT FUNDING

This invention was made with government support under EB013029 awarded by the National Institutes of Health. The government has certain rights in the invention.

TECHNICAL FIELD

This disclosure relates to devices requiring implantable lead anchoring, and in particular to generating fixation and stability feedback information for the implanted lead.

BACKGROUND

Implantable leads have numerous applications and are commonly used in medical devices to record electrical activity and/or stimulate a target site. An example of a widespread use of implantable leads in medical devices is in pacemaker or implantable cardioverter-defibrillator (ICD) implantations. Devices such as pacemakers are implanted into the heart as part of artificial cardiac pacing or cardiac resynchronization therapy, which involves generating electrical impulses that are carried by the pacing lead to the heart tissue fibers, signaling them to contract and relax properly. The implantable lead has a distal end and a proximal end. The distal end makes contact with the heart tissue and the proximal end is configured to make contact with the pacing pulse generator. Furthermore, at each end there are two electrical terminals. In particular, at the distal end there is a negative and a positive terminal, and at the proximal end there is a corresponding negative and a positive terminal. Therefore, the negative terminal of the distal end is electrically coupled to the negative terminal of the proximal end, and the positive terminal of the distal end is electrically coupled to the positive terminal of the proximal end. The positive terminals and negative terminals are electrically isolated from each other.

Pacemaker and implantable cardiac device (ICD) leads are anchored to tissue using a fixation mechanism. The lead is typically introduced into the venous system under the patient's collarbone, and its distal end is advanced toward the patient's heart by guiding the lead until the distal end has reached the desired heart wall location in the atrial or ventricular chamber.

There are two common types of fixation mechanisms used to anchor an ICD lead to tissue: active and passive fixation. The passive fixation mechanisms have a plurality of flexible tines that protrude from the distal end of the implantable lead. When the distal end of the lead is pushed into the cardiac tissue the tines latch onto the tissue in order to secure the fixation tip in place. Active fixation mechanisms, by contrast, have a corkscrew-like apparatus at the distal end of the lead which is retracted while the lead is guided to the heart. Once the clinician has determined the desired fixation position (using various imaging technologies and tactile feedback), current practice of anchoring the distal end of the lead to the heart wall involves using a disposable tool to turn a fixation pin at the proximal end of the lead. The clinician turns the pin a predetermined number of times causing advancement of the corkscrew-like apparatus at the distal end into the tissue. Using this method, the clinician attempts to ensure that the lead has an adequate hold on the tissue. The success of anchoring is determined based on several factors including tactile feedback, electrical measurements, and the overall experience of the clinician.

The tactile feedback method typically involves gently tugging on the proximal end of the lead, prior to taking electrical measurements. If the distal end remains secured, the clinician may be satisfied with anchoring. The tactile feedback method relies on subjective standards. The electrical measurement includes connecting the negative and positive terminals of the proximal end to an electrical measurement device. Here, various signals are communicated through the proximal end terminals to the distal end terminals enabling the measurement of conductivity, impedance, electrocardiogram (ECG) amplitudes, pacing thresholds, maximum output and slew rate at the distal end. While the electrical measurement method provides some objective data, it may be difficult to correlate the electrical data obtained from the measurement to how well the lead is anchored in the tissue. The clinician preference may include viewing the lead anchoring in the tissue via various imaging technologies, the tactile feedback method, and/or the electrical measurement method.

The above-described pacemaker implantation methods, however, can result in complications. Common complications include lead malposition (i.e., situations where the lead is not properly placed, potentially resulting in undesired lead penetration into the tissue) or migration (i.e., the lead has moved from the desired location). Lead migration can result in undesirable complications indicated by changes in conductivity which can increase pacing thresholds required to stimulate the heart, decreased sensing ability of the pacemaker, and can thus lead to decreased device performance or even life-threatening consequences. Perforation of the heart wall caused by lead penetration to the tissue can result in various complications, including pericardial effusion.

Aside from pacemakers and ICDs, there are a number of other applications of implantable leads. These applications include: spinal cord stimulators; spinal fusion stimulators; bone growth stimulators; implantable electrocardiogram systems; neuromodulation systems (for example, to be used in cochlear implants, vagus nerve stimulators, deep-brain stimulators, sacral nerve stimulation, implantable electromyography recording devices, migraine treatment, spinal cord injuries, and pain management); and subarachnoid stimulators. All these applications may include a lead anchoring in a respective tissue as described above. Similarly, these other applications may suffer from the same or similar complications as described above.

In view of the foregoing, there is an unmet need for a reliable and efficient system which can provide effective feedback for ensuring proper anchoring of an implantable lead into tissue.

SUMMARY

A lead fixation and stability feedback assembly for testing stability and anchoring of a fixation tip of a distal end of an implantable lead to a tissue is disclosed. The assembly includes a first member including a first coupling arrangement configured to couple to a proximal end of an implantable lead, wherein the proximal end of the implantable lead is coupled to a distal end of the implantable lead configured to be anchored to a tissue, and a second member including a second coupling arrangement configured to couple the first member to the second member, the second coupling arrangement configured to decouple the second member from the first member when a predetermined force is applied to pull the second member away from the first member to thereby test the anchoring of the distal end of the implantable lead to the tissue.

A method of testing anchoring and stability of an implantable lead to a tissue is also disclosed. The method includes anchoring a fixation tip of a distal end of the implantable lead into a tissue, providing a predetermined force to a second member coupled to a first member, the first member coupled to the proximal end of the implantable lead, and verifying the second member decouples from the first member when the predetermined force is applied.

BRIEF DESCRIPTION OF DRAWINGS

FIG. 6A illustrates a perspective view of a force scale arrangement as part of the alternate embodiment shown in FIG. 6 of the lead fixation and stability feedback assembly.

FIG. 6B illustrates a front view of the force scale shown in FIG. 6A.

FIG. 6C illustrates a schematic of an alternate embodiment of an alternative lead fixation and stability feedback mechanism including a tooth and a plurality of locking gears.

FIG. 7 illustrates a schematic of an alternate embodiment of the lead fixation and stability feedback assembly with a mechanical decoupling mechanism.

FIG. 8 illustrates a schematic of an alternate embodiment of the lead fixation and stability feedback assembly with an electromagnetic coupling mechanism.

FIG. 9 illustrates a schematic of an alternate embodiment of the lead fixation and stability feedback assembly with a lead clamp assembly that includes one or more magnets.

FIG. 10 illustrates a schematic of an alternate embodiment of the lead fixation and stability feedback assembly with a lead clamp assembly that includes one or more electromagnets.

DETAILED DESCRIPTION

Figure 1A:
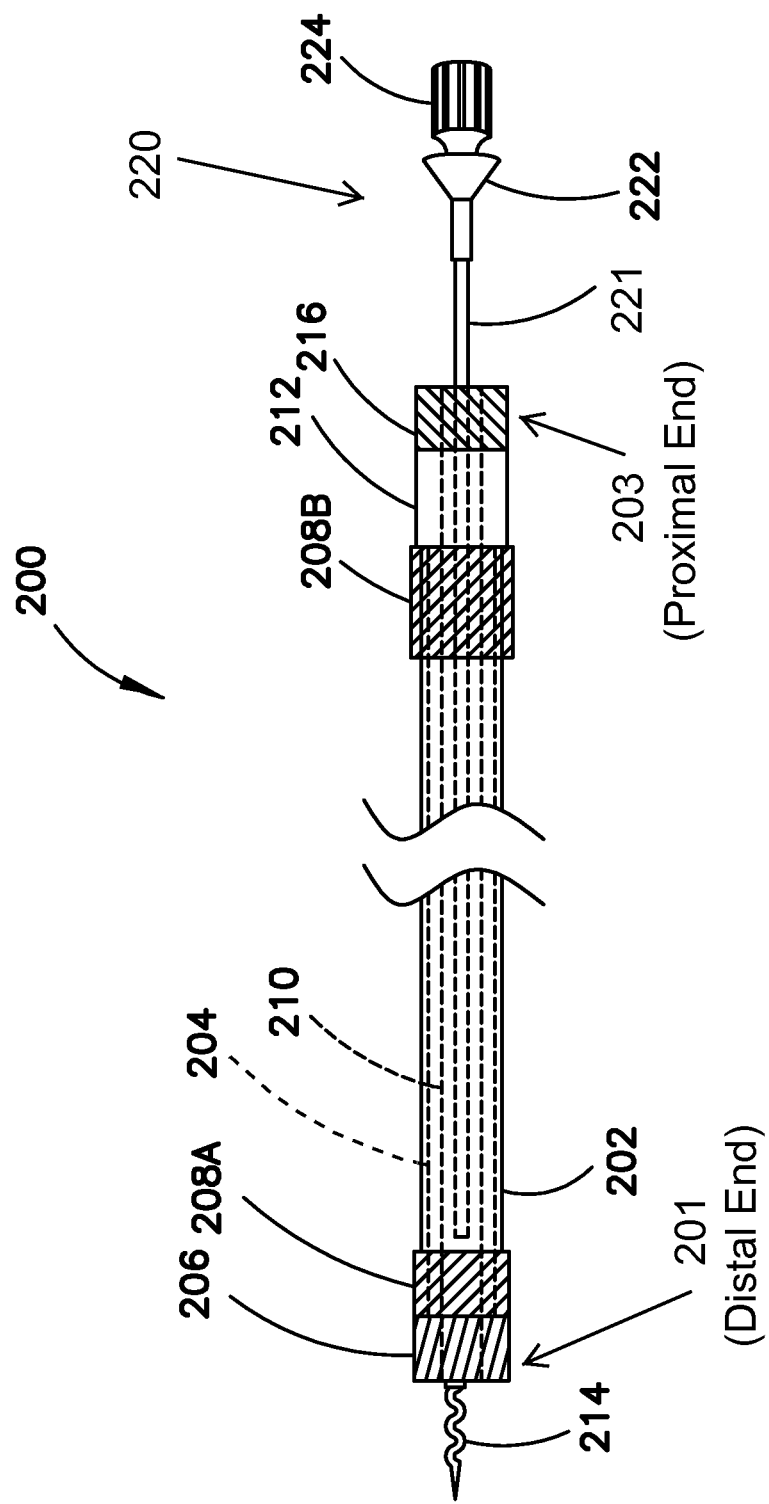
FIG. 1A illustrates a general implantable lead having a proximal end for sending and receiving electrical signals and a distal end for communicating the electrical signals to a tissue.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

The present disclosure provides methods and systems to address lead anchoring and stability complications described above by providing informative feedback to a clinician when implanting a lead in a tissue. It should be appreciated that tissue in the present disclosure applies to any biological, physiological, or synthetic material that is intended to represent human or animal tissue.

Implantable Lead

Referring to FIG. 1A, an implantable lead 200 is depicted. The implantable lead 200 comprises a distal end 201 coupled to a proximal end 203. The distal end 201 is configured to make contact with a tissue (not shown), with a fixation tip 214 configured to provide anchoring and coupling (mechanical and electrical) with the tissue (not shown). The implantable lead 200 further comprises a negative terminal coupling lead 204 disposed in between and configured to couple negative terminals 208A and 208B, a positive terminal coupling lead 210 disposed in between and configured to couple a positive terminal 216 and a fixation tip 214.

The implantable lead 200 further comprises electrically insulating members 206 and 212. The electrically insulating member 206 is disposed between and is configured to electrically isolate the negative terminal 208A from the fixation tip 214. The electrically insulating member 212 is disposed between and is configured to electrically isolate the negative terminal 208B from the positive terminal 216.

The positive terminal 216 while positioned next to the negative terminal 208B is configured to rotate with respect to the negative terminal 208B. Similarly, the fixation tip 214 while positioned next to the negative terminal 208A is configured to rotate with respect to the negative terminal 208A. By the coupling of the positive terminal 216 and the fixation tip 214 (via the positive terminal coupling lead 210), rotating the positive terminal 216 results in rotation of the fixation tip 214 with the negative terminals 208A and 208B substantially stationary. As will become apparent below, a lead fixation and stability feedback assembly 110 (see FIG. 1B) is configured to grip the positive terminal 216 and rotate it causing the fixation tip 214 to be advanced into a tissue (not shown).

The implantable lead 200 further comprises of a polymeric insulation sleeve 202 that extended from the distal side of the negative terminal 208B to the proximal side of the negative terminal 208A. The polymeric insulation sleeve 202 is configured to isolate the negative terminal coupling lead 204 and the remainder of the implantable lead 200 from its outside environment, both electrically and environmentally.

While note shown, the positive terminal coupling lead 210 and negative terminal coupling lead 204 are also electrically isolated from one another by an electrically isolating material.

The implantable lead 200 further comprises a stylet assembly 220. The stylet assembly 220 comprises a stylet wire 221, a stylet guide 222, and a stylet tip 224. The stylet guide 222 includes a through-hole configured to allow the stylet wire 221 to feed through. While the stylet tip 224 is affixed to the stylet wire 221, the stylet guide 222 is configured to slide over the stylet wire 221. The stylet assembly 220 is positioned inside the implantable lead 200 prior to the implantable lead 200 being positioned in the patient. The purpose of the stylet assembly 220 is to make it easier to guide the implantable lead 200 into the patient; and the purpose of the stylet guide 222 is to make it easier to feed the stylet wire 221 into the implantable lead 200. The stylet assembly 220 is configured to provide a degree of rigidity to the implantable lead 200, which without the stylet assembly is considerably flexible at the distal end 201.

As described above, electrical measurements to test lead functionality at the distal end 201 of the implantable lead 200, specifically between the fixation tip 214 and the negative terminal 208A, are taken at the proximal end, specifically between the positive terminal 216 and the negative terminal 208B.

Lead Fixation and Stability Feedback Assembly

Figure 1B:
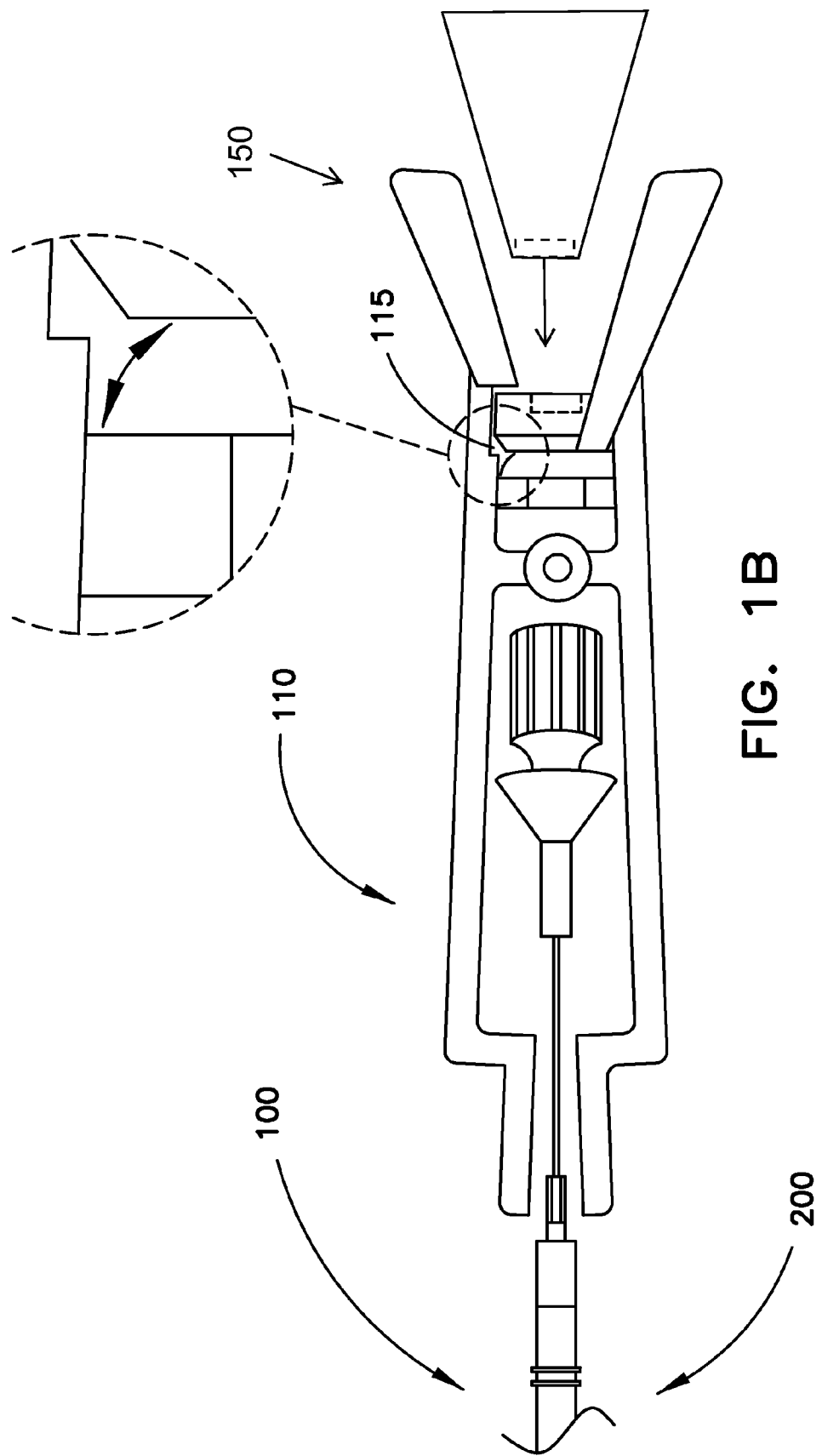
FIG. 1B illustrates a lead fixation and stability feedback assembly with a lead clamp assembly in an open position about the proximal end of the implantable lead presented in FIG. 1A.

Referring to FIG. 1B, a lead fixation and stability feedback system 100 is depicted. The lead fixation and stability feedback system 100 includes the lead fixation and stability feedback assembly 110 and the implantable lead 200. The lead fixation and stability feedback assembly 110 is depicted in an open position about the implantable lead 200. The open and closed positions of the lead fixation and stability feedback assembly 110 can be achieved by pressing on a second handle 120B against a first handle 120A (depicted in FIG. 2), or releasing the second handle 120B causing opening and closing of a lead clamp assembly 140 (See FIG. 2). Arrows 115 depict the relative movement of the second handle 120B into the open position. Also depicted in FIG. 1B is a decoupling assembly 150 further described below (See FIGS. 2, 3, and 4). The decoupling assembly 150 is depicted in a decoupled state in FIGS. 1B and 2, while it is depicted in a coupled state in FIG. 3.

Figure 2:
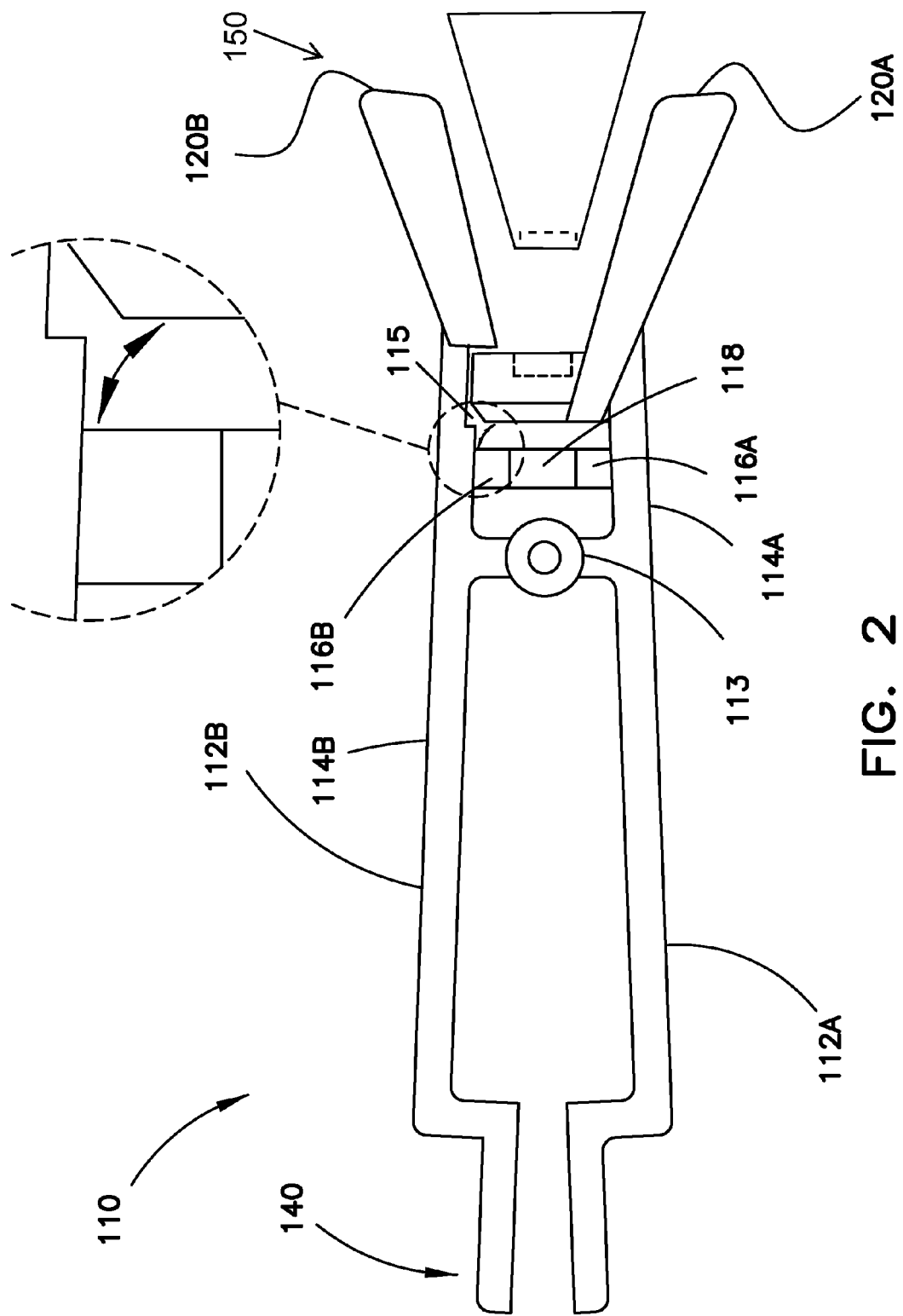
FIG. 2 illustrates a side view of the lead fixation and stability feedback assembly with a magnetic coupling arrangement.
Figure 3:
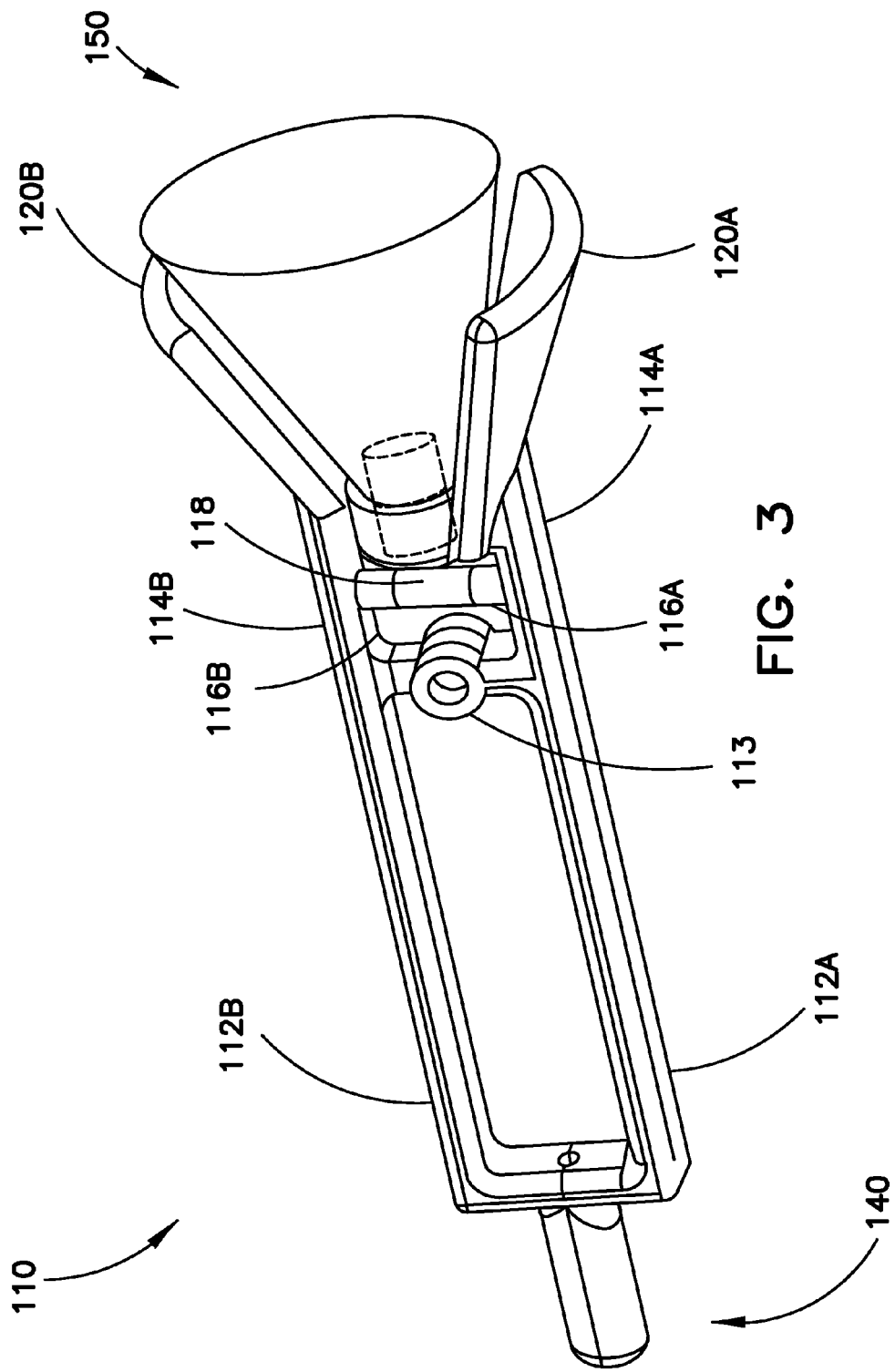
FIG. 3 illustrates a perspective view of the lead fixation and stability feedback assembly, with the lead clamp assembly in a closed position.

Referring to FIGS. 2 and 3, a side view and a perspective view of the lead fixation and stability feedback assembly 110 are depicted in the open and closed positions, respectively. The lead fixation and stability feedback assembly 110 comprises a lead clamp assembly 140, a distal first arm 112A coupled to a proximal first arm 114A, a distal second arm 112B coupled to a proximal second arm 114B, a biasing member 118, a first handle 120A, and a second handle 120B. A fulcrum 113 couples the distal first arm 112A, the proximal first arm 114A, the distal second arm 112B, and the proximal second arm 114B together allowing relative movements of a combination of the distal first arm 112A and the proximal first arm 114A as one solid member with respect to a combination of the distal second arm 112B and the proximal second arm 114B as another solid member. The biasing member 118, e.g., a spring, is coupled to a first biasing member connector 116A and a second biasing member connector 116B. The first biasing member connector 116A is coupled to the proximal first arm 114A and the second biasing member connector 116B is coupled to the proximal second arm 114B. The first handle 120A is coupled to the proximal first arm 114A and the second handle 120B is coupled to the proximal second arm 114B. In FIG. 2, the double arrows 115 again depict the movement of the second handle 120B to achieve the open position. It should be noted that when in the closed position, the spacing denoted by the double arrows 115 is enlarged (See FIG. 4).

The lead fixation and stability feedback assembly 110 further includes a decoupling assembly 150 disposed on the proximal end of the lead fixation and stability feedback assembly 110 opposing the distal end where the lead clamp assembly is positioned.

Figure 4:
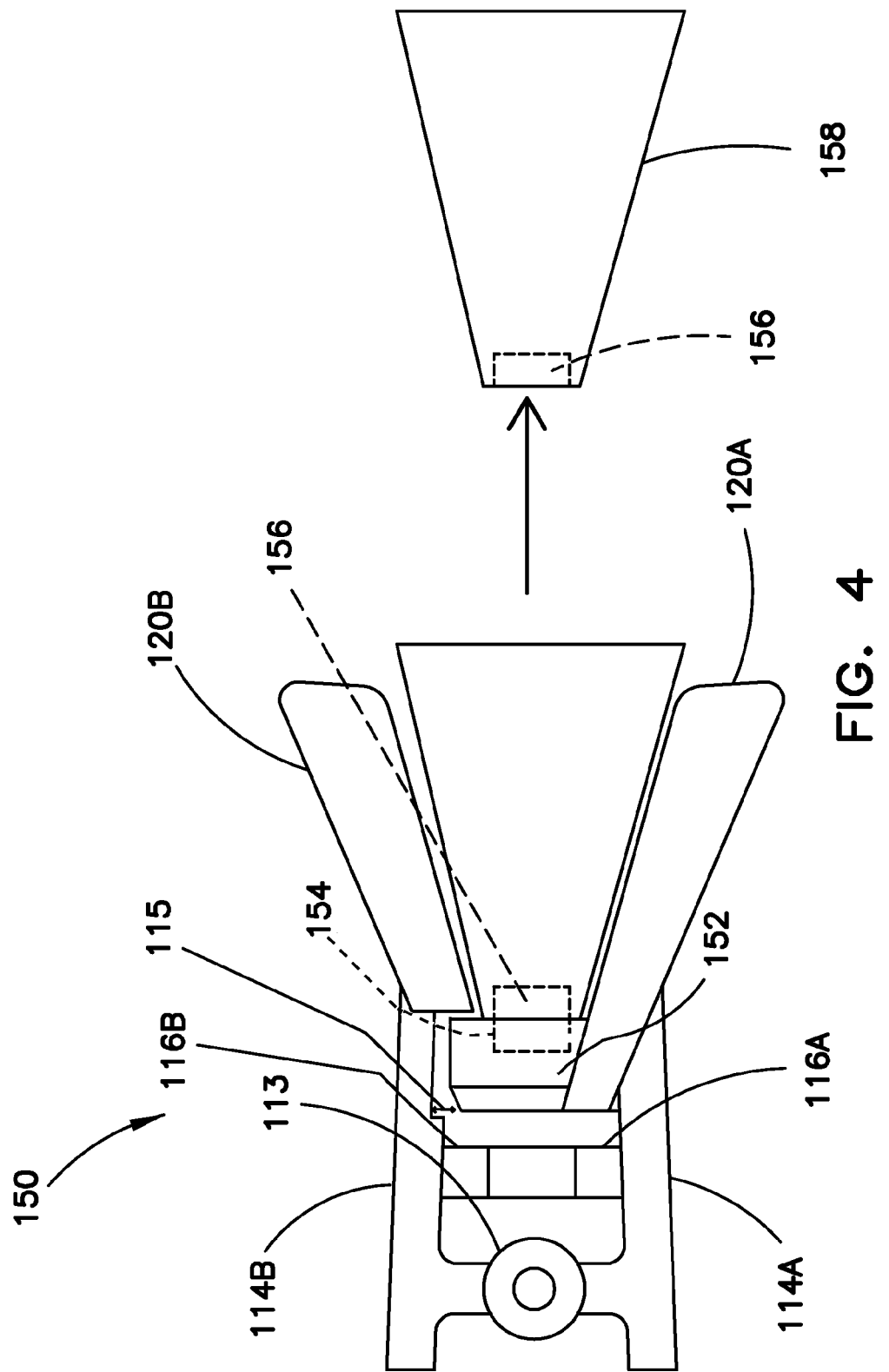
FIG. 4 illustrates a side view of a proximal end of the lead fixation and stability feedback assembly depicting decoupling of a proximal feedback member of the lead fixation and stability feedback assembly.

Referring to FIG. 4, a side view of the decoupling assembly 150 is depicted with respect to the proximal end of the lead fixation and stability feedback assembly 110. The decoupling assembly 150 comprises a proximal feedback member 158 coupled to a proximal decoupling device 156 and a distal feedback member 152 coupled to a distal decoupling device 154. The proximal decoupling device 156 is coupled to the distal decoupling device 154. In the embodiment depicted in FIG. 4, the proximal decoupling device 156 and the distal decoupling device 154 are both magnets. As illustrated in FIG. 4, the proximal decoupling device 156 is configured to decouple from the distal decoupling device 154 upon application of a predetermined amount of decoupling force applied axially. The predetermined amount of decoupling force is determined according to the specific application of the implantable lead 200. The interface should be designed such that when the decoupling force is applied to the proximal decoupling device 156 from 0 N to the predetermined force, the proximal decoupling device 156 maintains contact with the distal decoupling device 154 until the predetermined force is reached at which point the proximal decoupling device 156 separates from the distal decoupling device 154. The predetermined force according to the embodiment depicted in FIG. 4 for a pacemaker application using an active fixation apparatus is about 0.9 N+/−0.1 N. Attaining the predetermined force level indicates adequate anchoring of the implantable lead 200 to the tissue (not shown). Therefore, exerting a decoupling force up to 0.9 N+/−0.1 N should not cause a premature separation between the proximal decoupling device 156 and the distal decoupling device 154. It should be appreciated, however, that the predetermined force of 0.9 N+/−0.1 N is based on a cardiac application and further based on the type of fixation tip 214 (See FIG. 1A). It should be noted that the predetermined force is based on one application. Furthermore, it should be appreciated that insertion of the fixation tip in a non-cardiac muscle tissue, e.g., into bone, cartridge, or brain tissue, will require different predetermined force levels. By choosing different pairs of the proximal decoupling device 156 and the distal decoupling device 154, different predetermined force levels can be realized.

It should further be noted that when the lead fixation and stability feedback assembly 110 is in the closed position and the proximal feedback member 158 is placed adjacent and coupled to the distal feedback member 152 (as depicted in FIG. 3), the proximal feedback member 158 prevents relative movement of the second handle 120B to avoid inadvertent placing the lead fixation and stability feedback assembly 110 in the open position. Therefore, in order to move the second handle 120B, the proximal feedback member 158 must first be removed.

Figure 5:
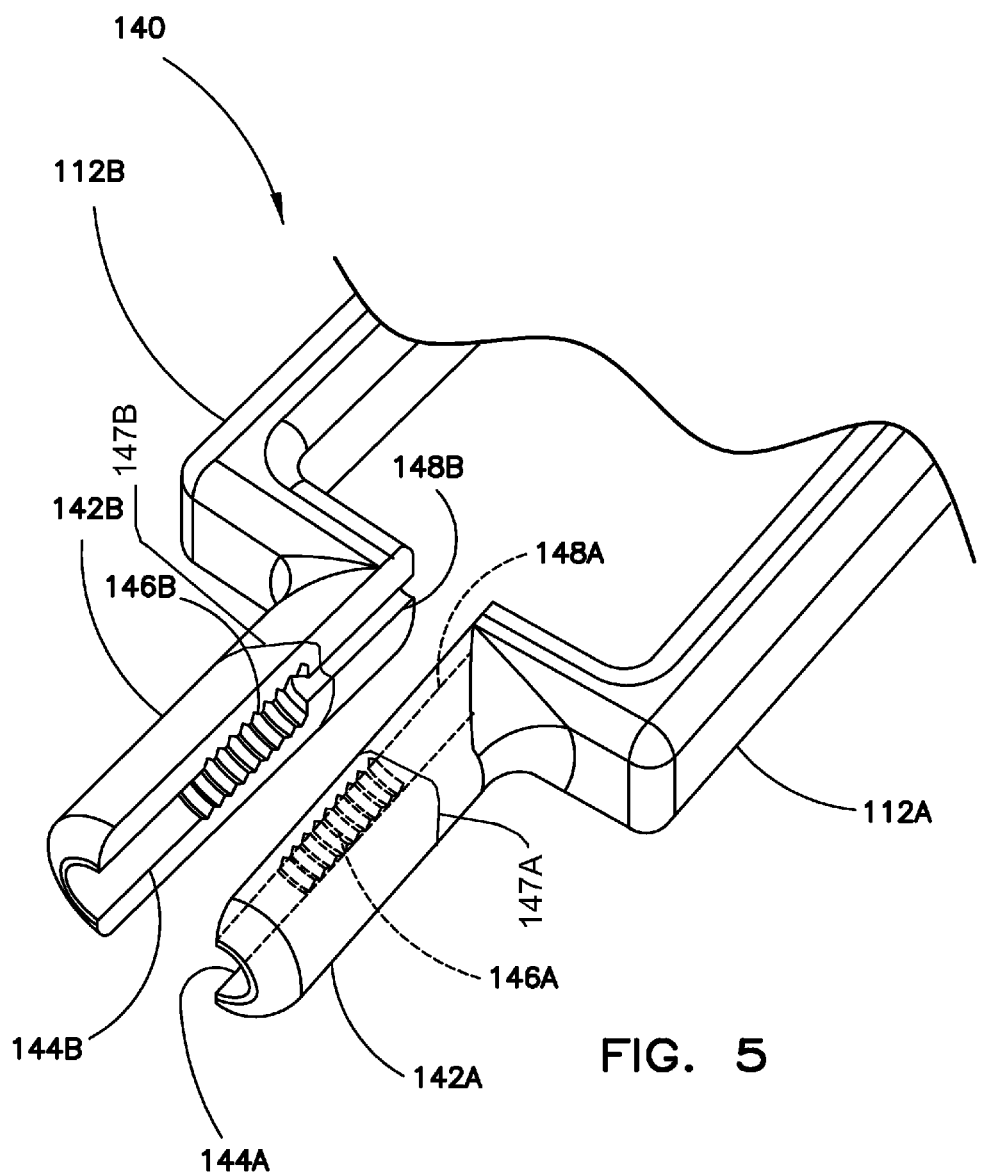
FIG. 5 illustrates a perspective view of the lead clamp assembly in the open position.

Referring to FIG. 5, a perspective view of one embodiment of the lead clamp assembly 140 is depicted in an open position. The lead clamp assembly 140 includes a first jaw 142A and a second jaw 142B. The first jaw 142A is coupled to the distal first arm 112A and the second jaw 142B is coupled to the distal second arm 112B. The first jaw 142A and the second jaw 142B are configured to be disposed on the proximal end 203 of the implantable lead 200 (See FIG. 1A). The first jaw 142A in FIG. 5 includes terminal jaw sections 148A and 144A, configured to be disposed on and electrically coupled to the positive terminal 216 and the negative terminal 208B, respectively, of the implantable lead 200 (see FIG. 1A). The first jaw 142A of FIG. 5 further includes a grooved jaw section 146A, approximately centered with respect to the terminal jaw sections 148A and 144A, and configured to be disposed and mechanically coupled to the electrically insulating member 212. Furthermore, the grooved jaw section 146A is configured to electrically isolate terminal jaw sections 148A and 144A. Similarly, the second jaw 142B includes terminal jaw sections 148B and 144B, configured to be disposed on and electrically coupled to the positive terminal 216 and the negative terminal 208B, respectively, of the implantable lead 200 (see FIG. 1A). The second jaw 142B further includes a grooved jaw section 146B, approximately centered with respect to the terminal jaw sections 148B and 144B, and configured to be disposed and mechanically coupled to the electrically insulating member 212. Furthermore, the grooved jaw section 146B is configured to electrically isolate terminal jaw sections 148B and 144B.

In order for the lead clamp assembly 140 to be able to both rotate the positive terminal 216 and yet make electrical measurements by coupling to the negative terminal 208B, not only do the jaw sections 148A and 148B have to be electrically isolated from the jaw sections 144A and 144B, respectively, the jaw sections 148A and 148B have to be mechanically isolated from the remainder of the first and second jaws 142A and 142B, respectively. In other words, the jaw sections 148A and 148B and the remainder of the lead clamp assembly 140 to the right of the jaw sections 148A and 148B (as depicted in FIG. 5) are configured to rotate while the grooved jaw sections 146A and 146B and the jaw sections 144A and 144B remain stationary. Accordingly, break lines 147A and 147B are depicted in FIG. 5 to illustrate a break between the respective sections of the first and second jaws 142A and 142B.

Figure 6:
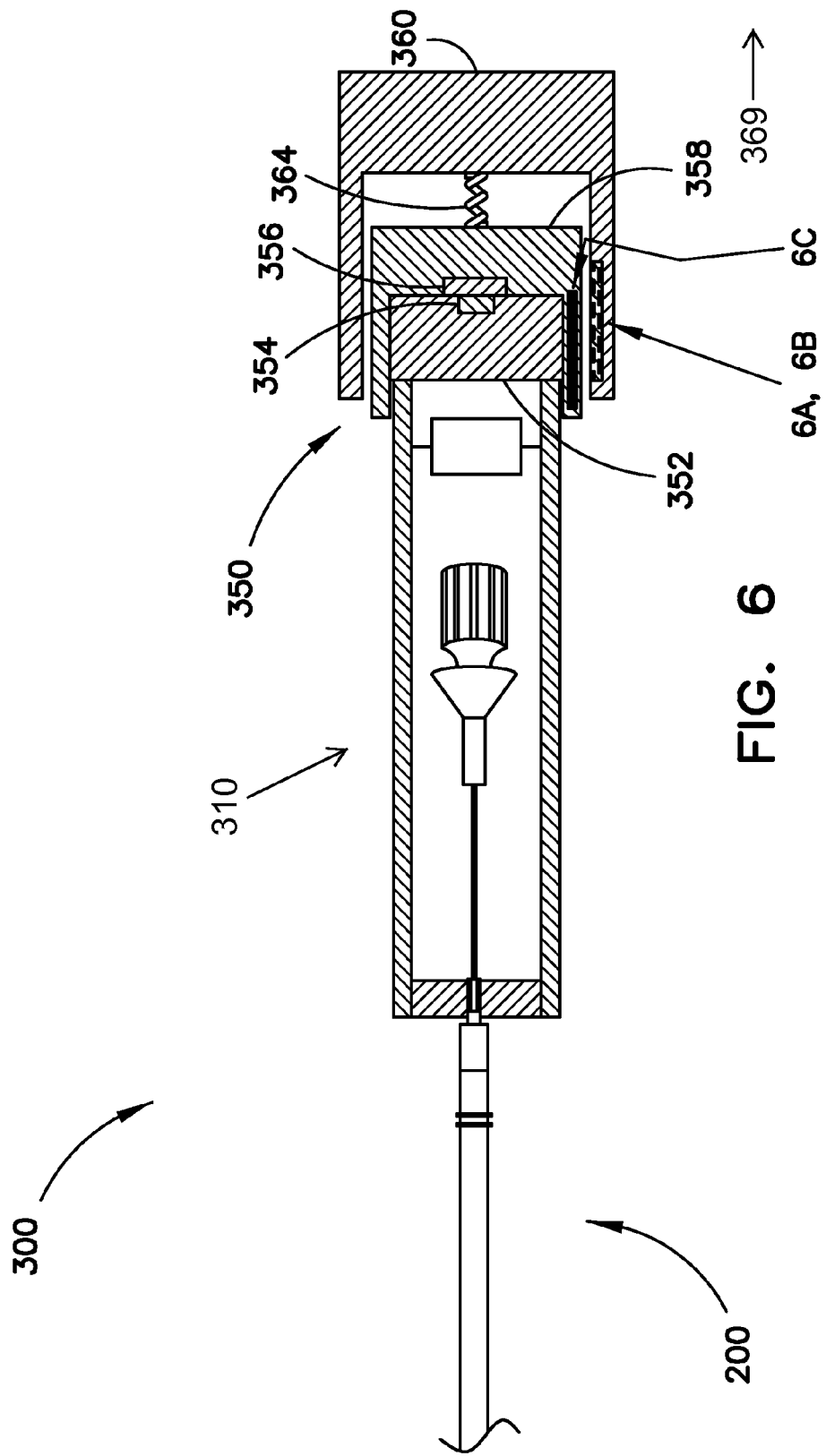
FIG. 6 illustrates a schematic of an embodiment of the lead fixation and stability feedback assembly that includes a biased coupling arrangement.

While not shown, in an alternative embodiment, the lead clamp assembly 140 can be provided without the jaw sections 144A and 144B and the grooved jaw sections 146A and 146B. In this embodiment, an example of which is depicted in the schematic of FIG. 6, the jaw sections 148A and 148B are the only extruding members of the first and second jaws 142A and 142B.

Figure 11:
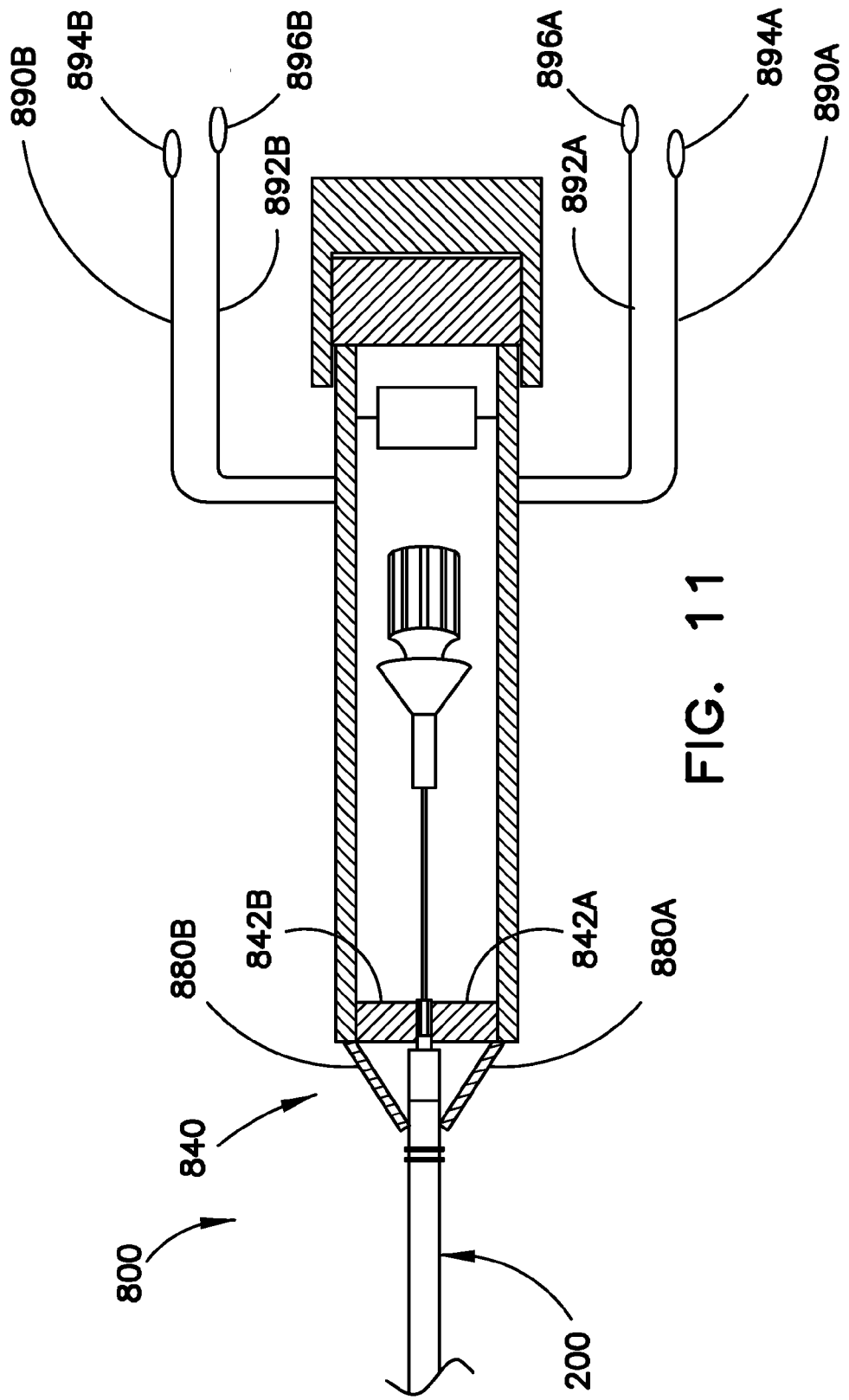
FIG. 11 illustrates a schematic of an alternate embodiment of the lead fixation and stability feedback assembly which includes electrical terminals.

While not shown in FIG. 5, jaw sections 144A, 144B, 148A, and 148B can be coupled to four lead wires (See FIG. 11). The lead wires can be reduced down to two by internally connecting each set of lead wires, as further described below.

There are two positions (open and closed) shown in FIGS. 2 and 3. As described above, when a force is applied to the first and second handles 120A and 120B, in order to move the second handle 120B which is movable towards the first handle 120A which is stationary, the lead fixation and stability feedback assembly 110 can be moved from the closed position (see FIG. 3) to the open position (See FIG. 2). As described below in the operation portion of the present disclosure, when in the open position, the lead clamp assembly 140 can be placed over the positive terminal 216, the electrically insulating member 212, and the negative terminal 208B (according to the embodiment of the lead clamp assembly 140 shown in FIG. 5), or only over the positive terminal 216 (according to the embodiment of the lead clamp assembly depicted in the schematic of FIG. 6); and once properly positioned, the force holding the lead clamp assembly 140 in the open position removed to allow the lead clamp assembly 140 to grip the positive terminal 216, the insulating member 212 and the negative terminal 208B (or just the positive terminal 216 depending on which lead clamp assembly 140 is used in the embodiments depicted in FIGS. 5 and 6). The resulting position (not shown) is henceforth referred to as a pseudo-closed position. In the pseudo-closed position, the first and second jaws 142A and 142B are securely gripping the positive terminal 216, the insulating member 212, and the negative terminal 208B. As described above, the grooved jaw sections 146A and 146B are configured to mechanically grip the electrically insulating member 212 in order to prevent relative movement between the lead clamp assembly 140 and the positive terminal 216 when the decoupling force is being applied to the proximal decoupling device 156 and when the lead clamp assembly 140 is in the pseudo-closed position.

Figure 5A:
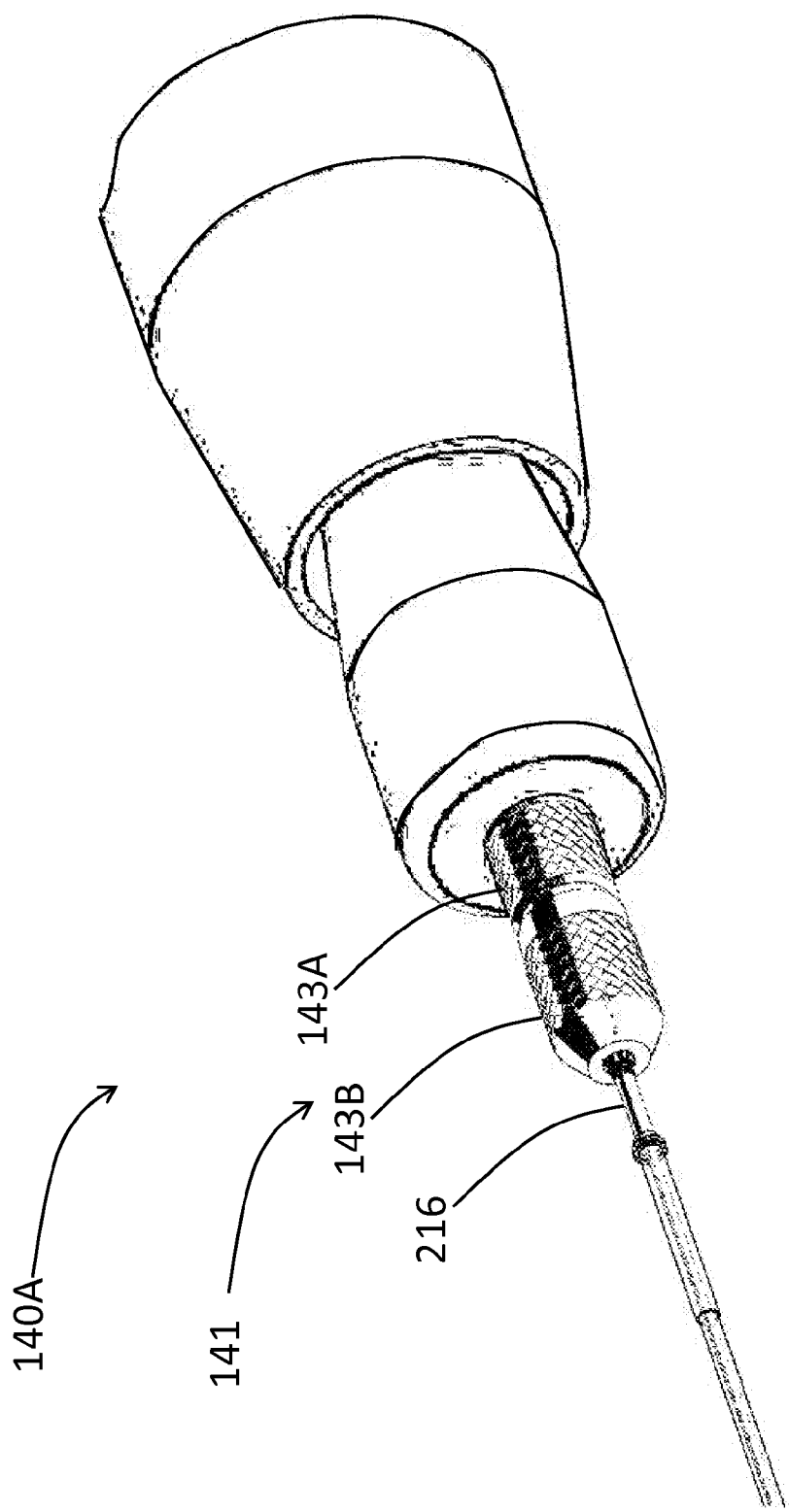
FIG. 5A illustrates a side view of a lead fixation and stability feedback assembly with an alternate lead clamp assembly having a pin-vise lead attachment mechanism depicted in a closed position.

Referring to FIG. 5A, a perspective view of an alternative embodiment of a lead clamp assembly 140A is depicted. The lead clamp assembly 140A includes a pin-vise lead attachment mechanism 141 which includes tightening members 143A and 143B (as is known to a person having ordinary skill in the art). The tightening member 143B is configured to rotate with respect to tightening member 143A, thereby allowing the pin-vise lead attachment mechanism 141 to tightly grip the positive terminal 216. In this embodiment, the stylet assembly 220 has been removed to avoid interference with the lead clamp assembly 140A.

Referring to FIG. 6, a schematic of another embodiment of a lead fixation and stability feedback system 300 is depicted. The lead fixation and stability feedback system 300 includes the implantable electric lead 200 and a lead fixation and stability feedback assembly 310. The lead fixation and stability feedback assembly 310 is similar to the lead fixation and stability feedback assembly 110, with the exception that its corresponding lead fixation and stability feedback mechanism 350, in addition to its corresponding distal feedback member 352, distal decoupling device 354, proximal feedback member 358, and proximal decoupling device 356, includes a force feedback member 360 and a biasing member 364. As with the lead fixation and stability feedback mechanism 150 (see FIG. 4), the distal decoupling device 354 of the lead fixation and stability feedback mechanism 350 is coupled to a distal feedback member 352. The distal decoupling device 354 is further coupled to the proximal decoupling device 356. The proximal decoupling device 356 is coupled to the proximal feedback member 358. A predetermined force is needed to separate the proximal decoupling device 356 from the distal decoupling device 354.

The proximal feedback member 358 is coupled to the force feedback member 360 by the biasing member 364. According to spring mechanics principles, when the force feedback member 360 is axially pulled in the direction of arrow 369 from the proximal feedback member 358, a linearly increasing force is translated on the proximal feedback member 358. Once the force reaches the predetermined force, the distal decoupling device 354 and the proximal decoupling device 356 decouple. Attaining the predetermined force level indicates adequate anchoring of the implantable lead 200 to the tissue (not shown).

Referring to FIGS. 6A and 6B, schematics of an alternative lead fixation and stability feedback mechanism 350 embodiment is depicted. The lead fixation and stability feedback mechanism 350 may include a digital/analog force indicator 380 which may include a force scale 382 (See FIG. 6B) disposed on the proximal feedback member 358, displayed in a scale window 370 (See FIG. 6A) disposed on the force feedback member 360. The force scale 382 permits the clinician to have additional quantitative feedback through the digital/analog scale indicator 380 with a force indicator 388 to indicate the level of force that is exerted and how much force is required to cause the distal decoupling device 354 to decouple from the proximal decoupling device 356. In addition, an optional first indicator 384 and an optional second indicator 386, or a plurality thereof, may be placed on the force scale 382. This optional first indicator 384 and optional second indicator 386 may be in the form of light emitting diodes configured to indicate when the predetermined force level has been attained. While the necessary control system to activate the optional first indicator 384 and the optional second indicator 386 has not been discussed, such a control system is known to a person having ordinary level of skill in the art.

In yet another embodiment, referring to FIG. 6C, a schematic of a ratchet-like mechanism in an alternate embodiment of the lead fixation and stability feedback mechanism 350 is depicted. The ratchet-like mechanism may include a plurality of teeth 387 which are attached to the proximal feedback member 358, with an L-shaped member 390 attached to the force feedback member 360, configured to slide along the plurality of teeth 387 in proportion to the force level exerted on the biasing member 364. The ratchet-like mechanism ensures forward movement according to arrow 391, and accordingly prevents reverse movement unless a release mechanism is activated (known to a person having ordinary skill in the art) to pull the L-shaped member 390 away from the teeth 387 and allowing the biasing member 364 to reverse the force feedback member 360 to move in a direction opposite that of the arrow 391. With respect to the cardiac pacemaker example discussed above, when the L-shaped member 390 is approximately near the tooth 387 marking 0.9 N, the predetermined force is attained resulting in the decoupling of the proximal and distal decoupling devices 356 and 354, respectively.

Referring to FIG. 7, a schematic of another embodiment of a lead fixation and stability feedback system 400 is depicted. The lead fixation and stability feedback system 400 includes the implantable electric lead 200 and a lead fixation and stability feedback assembly 410. The lead fixation and stability feedback assembly 410 is similar to the lead fixation and stability feedback assembly 110, with the exception that its corresponding lead fixation and stability feedback mechanism 450, in addition to its corresponding distal feedback member 452 and proximal feedback member 458, includes a first decoupling device 462, a second decoupling device 460, and a mechanical decoupling member 464. As with the lead fixation and stability feedback mechanism 150 (see FIG. 4), the first decoupling device 462 of the lead fixation and stability feedback mechanism 450 is coupled to the distal feedback member 452. The first decoupling device 462 is further coupled to the second decoupling device 460 via the mechanical decoupling member 464. The second decoupling device 460 is coupled to the proximal feedback member 458. A predetermined force is needed to break the mechanical decoupling member 464 allowing separation of the second decoupling device 458 from the first decoupling device 452.

Referring to FIG. 8, a schematic of another embodiment of a lead fixation and stability feedback system 500 is depicted. The lead fixation and stability feedback system 500 includes the implantable electric lead 200 and a lead fixation and stability feedback assembly 510. The lead fixation and stability feedback assembly 510 is similar to the lead fixation and stability feedback assembly 110, with the exception that its corresponding lead fixation and stability feedback mechanism 550, in addition to its corresponding distal feedback member 552 and proximal feedback member 558, includes a first decoupling device 562 and a second optional decoupling device 560. As with the lead fixation and stability feedback mechanism 150 (see FIG. 4), the first decoupling device 562 of the lead fixation and stability feedback mechanism 550 is coupled to the distal feedback member 552. The first decoupling device 562 is further coupled to the second optional decoupling device 560. The second optional decoupling device 560 is coupled to the proximal feedback member 558. A predetermined force is needed to separate the proximal feedback member 558 from the distal feedback member 552. The first decoupling device 562 and the second optional decoupling device 560 are electromagnetic decoupling devices, where wire winding 563 about a core (not shown) generates an electromagnetic attraction with the second optional decoupling device 560, having a respective winding 565 about a core (not shown), or an attraction with the proximal feedback member 558 in the absence of the second optional decoupling device 560.

Referring to FIG. 9, a schematic of another embodiment of a lead fixation and stability feedback system 600 is depicted. The lead fixation and stability feedback system 600 includes the implantable electric lead 200 and an alternate lead clamp assembly 640. The lead clamp assembly 640 depicted in the pseudo-closed position includes first and second jaws 642A and 642B, each including a magnet 646A and 646B, respectively. It should be appreciated that in FIG. 9, the jaws 642A and 642B are depicted as only making contact with the positive terminal 216 (See FIG. 1A). The magnets are intended to provide further gripping force on the positive terminal 216 to ensure no inadvertent relative movement occurs between the positive terminal 216 and the lead fixation and stability feedback system 600. As discussed in FIG. 8, one of the magnets 646A or 646B can be optional, where in the absence of it, the magnetic attraction is between the other magnet and the opposite jaw.

Referring to FIG. 10, a schematic of another embodiment of a lead fixation and stability feedback system 700 is depicted. The lead fixation and stability feedback system 700 includes the implantable electric lead 200 and an alternate lead clamp assembly 740. The lead clamp assembly 740 depicted in the pseudo-closed position includes first and second jaws 742A and 742B, each including an electromagnet 746A and 746B, respectively. It should be appreciated that in FIG. 10, the jaws 742A and 742B are depicted as only making contact with the positive terminal 216 (See FIG. 1A). The electromagnets are intended to provide further gripping force on the positive terminal 216 to ensure no inadvertent relative movement occurs between the positive terminal 216 and the lead fixation and stability feedback system 700.

Referring to FIG. 11, a schematic of another embodiment of a lead fixation and stability feedback system 800 is depicted. The lead fixation and stability feedback system 800 includes the implantable electric lead 200 and an alternate lead clamp assembly 840. The lead clamp assembly 840 depicted in the pseudo-closed position includes first and second jaws 842A and 842B, respectively. Coupled to each jaw but electrically isolated is a set of spring-loaded tines 880A and 880B, configured to make contact with the negative terminal 208B (See FIG. 1A). The jaws 842A and 842B are electrically coupled to lead wires 892A and 892B, respectively, which terminate at terminals 896A and 896B, respectively. The spring-loaded tines 880A and 880B are electrically coupled to lead wires 890A and 890B, respectively, which terminate at terminals 894A and 894B, respectively. The four lead wires and associated terminals can be reduced to two lead wires and terminals by internally electrically coupling matching lead wires.

It should be appreciated that while two magnets referenced as decoupling devices are depicted in the figures of the present disclosure, in one embodiment one such decoupling device can be used which may be positioned in either of the feedback members. For example, with regards to FIG. 4, it should be appreciated that a desired magnetic coupling can be generated with only the distal decoupling device 154 disposed in the distal feedback member 152 without the proximal decoupling device (referenced as 156) being placed in the distal feedback member 158.

Operation

Figure 12:
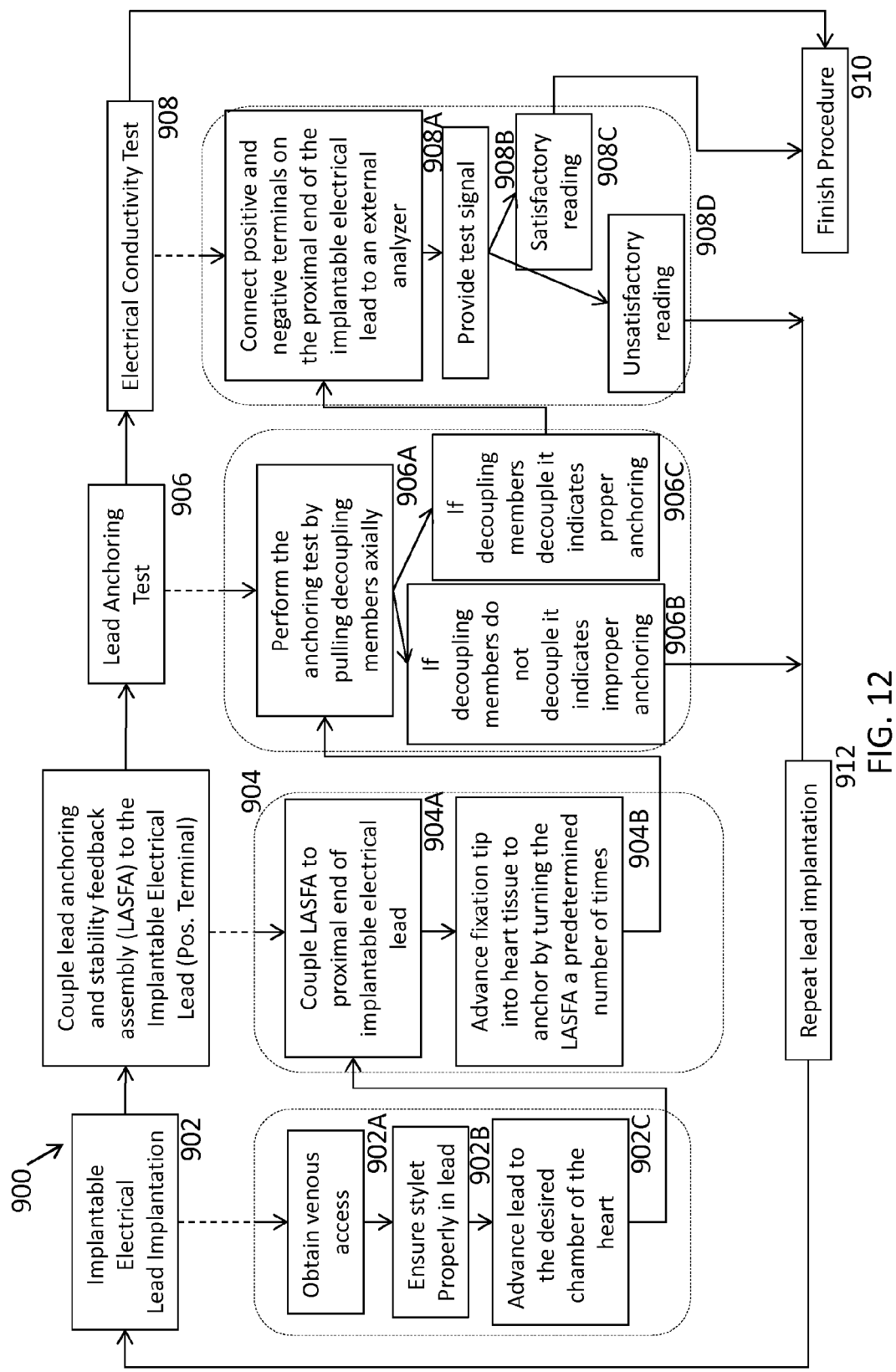
FIG. 12 illustrates a flow chart describing a method of using the lead fixation and stability feedback assembly.

Referring to FIG. 12, a process flow 900 illustrating a method for assuring adequate anchoring and stability of an implantable lead to a tissue is presented. According to FIG. 12, an implantable lead is first implanted (see blocks 900, 902A, 902B, and 902C). The presently disclosed lead fixation and stability feedback assembly is then coupled to the implantable lead. Using the lead fixation and stability feedback assembly, the anchoring of the implantable lead to the tissue is tested (See blocks 904, 904A, 904B, and 904C, 906, 906A, 906B, and 906C). If decoupling occurs between the decoupling members (e.g., 152 and 158, See FIG. 4) of the lead fixation and stability feedback assembly at a force level indicating an adequate anchoring, then the anchoring is deemed appropriate. Verification of the electrical measurements may then be performed after leads (See FIG. 11) have been connected to an external electrical measurement system (not shown) in order to provide needed signals for the electrical testing (See blocks 908, 908A, 908B, 908C, and 908D). Once the electrical conductivity and other electrical parameters (discussed above) are verified, the lead fixation and stability feedback assembly may be removed from the implantable lead, the stylet assembly removed, and the implantable lead may be coupled to the pacemaker (See block 910). If the lead implantation is deemed to have been unsatisfactory, e.g., premature decoupling of the implantable lead by applying force to the proximal decoupling member or improper electrical test reading, then the lead implantation is repeated (See block 912).

While the invention has been described with reference to certain embodiments, it will be apparent to those of ordinary skill in the art that other embodiments and implementations are possible that are within the scope of the invention without departing from the spirit and scope of the invention. It is therefore intended that the foregoing detailed description be regarded as illustrative rather than limiting.

The invention claimed is:

1. A lead fixation and stability feedback assembly for testing stability and anchoring of a fixation tip of a distal end of an implantable lead to a tissue, comprising:
   a first member including a first coupling arrangement configured to couple to a proximal end of an implantable lead, wherein the proximal end of the implantable lead is coupled to a distal end of the implantable lead configured to be anchored to a tissue, first coupling arrangement including a lead clamp assembly configured to translate one or more of a mechanical force and a magnetic force to grip the proximal end of the implantable lead; and
   a second member including a second coupling arrangement configured to couple the first member to the second member, the second coupling arrangement configured to decouple the second member from the first member when a predetermined force is applied to pull the second member away from the first member to thereby test the anchoring of the distal end of the implantable lead to the tissue.

2. The system of claim 1, the lead clamp assembly including gripping members configured to translate mechanical forces from a biasing member to grip the proximal end of the implantable lead.

3. The system of claim 1, the lead clamp assembly including a magnetic arrangement configured to provide magnetic attraction forces to grip the proximal end of the implantable lead.

4. The system of claim 3, the lead clamp assembly further including gripping members configured to translate mechanical forces from a biasing member to grip the proximal end of the implantable lead.

5. The system of claim 1, the lead clamp assembly including an electromagnetic arrangement configured to provide magnetic attraction forces to grip the proximal end of the implantable lead.

6. The system of claim 5, the lead clamp assembly further including gripping members configured to translate mechanical forces from a biasing member to grip the proximal end of the implantable lead.

7. The system of claim 1, the second coupling arrangement including at least one magnet disposed in one of the first or second members, configured to provide a magnetic attraction force between the first member and the second member, the magnetic attraction force configured to be about the predetermined force.

8. The system of claim 1, the second coupling arrangement including a first magnet disposed in the first member and a second magnet disposed in the second member, the first and second magnets configured to provide a magnetic attraction force between the first member and the second member, the magnetic attraction force configured to be about the predetermined force.

9. The system of claim 1, the second coupling arrangement including a mechanical decoupling member configured to break with a force about the predetermined force.

10. The system of claim 1, the second coupling arrangement including an electromagnetic interface disposed in the first member, the electromagnetic interface configured to provide a magnetic attraction force between the first member and the second member, the magnetic attraction force configured to be about the predetermined force.

11. A lead fixation and stability feedback assembly for testing stability and anchoring of a fixation tip of a distal end of an implantable lead to a tissue, comprising:
    a first member including a first coupling arrangement configured to couple to a proximal end of an implantable lead, wherein the proximal end of the implantable lead is coupled to a distal end of the implantable lead configured to be anchored to a tissue;
    a second member including a second coupling arrangement configured to couple the first member to the second member, the second coupling arrangement configured to decouple the second member from the first member when a predetermined force is applied to pull the second member away from the first member to thereby test the anchoring of the distal end of the implantable lead to the tissue;
    an electrical measurement arrangement including at least one electrical test lead coupled to the fixation tip of the implantable lead and at least one electrical test lead coupled to a return terminal at the distal end of the implantable lead, the two leads configured to provide a signal to measure electrical performance between the fixation tip and the return terminal.

12. A method of testing anchoring and stability of an implantable lead to a tissue, comprising:

anchoring a fixation tip of a distal end of the implantable lead into a tissue;

providing a predetermined force to a second member coupled to a first member, the first member coupled to the proximal end of the implantable lead; and verifying the second member decouples from the first member prior to reaching the predetermined force.

13. The method of claim 12, further comprising measuring electrical performance and impedance between the fixation tip and a return terminal positioned at the distal end of the implantable lead.

14. The method of claim 13, further comprising repeating the anchoring, providing a predetermined force, and the verifying steps if the electrical measurement falls outside of predetermined limits.

15. The method of claim 12, further comprising repeating the anchoring, providing a predetermined force, and the verifying steps if the verifying step resulted in movement of the second member while the proximal end of implant lead is still coupled to the first member.

16. The method of claim 12, the second member and the first member are coupled by at least one magnet, configured to provide a magnetic attraction force between the first member and the second member, the magnetic attraction force configured to be about the predetermined force.

17. The method of claim 12, the second member coupled to the first member by a coupling arrangement including a mechanical decoupling member configured to break with a force about the predetermined force.

18. The method of claim 12, the second member and the first member are coupled by an electromagnetic interface disposed in the first member, the electromagnetic interface configured to provide a magnetic attraction force between the first member and the second member, the magnetic attraction force configured to be about the predetermined force.

* * * * *